United States Patent [19]

Srivastava et al.

[11] Patent Number: 5,214,135
[45] Date of Patent: May 25, 1993

[54] N-PROTECTED-2'-O-METHYL-RIBONU-CLEOSIDES AND N-PROTECTED 2'-O-METHYL-3'-CYANOETHYL-N-,N-DIISOPROPYL PHOSPHORAMIDITE RIBONUCLEOSIDES

[75] Inventors: Suresh C. Srivastava, Burlington; Saroj K. Roy, Waltham, both of Mass.

[73] Assignee: ChemGenes Corporation, Waltham, Mass.

[21] Appl. No.: 753,077

[22] Filed: Aug. 30, 1991

[51] Int. Cl.$^5$ .......................................... C07H 19/167
[52] U.S. Cl. ................................ 536/26.7; 536/27.81; 536/26.71; 536/26.8; 536/28.5
[58] Field of Search ........................ 536/24, 26, 27, 28

[56] References Cited

U.S. PATENT DOCUMENTS 4,500,707  2/1985  Caruthers et al. ................... 536/27

OTHER PUBLICATIONS

Gaffney et al., "Synthesis and Characterization of a Set of Four Dodecadeoxyribonucleoside Undecaphosphates Containing O$^6$-Methylguanine opposite Adenine, Cytosine, Guanine, and Thymine", Biochemistry, 23, 5696-5691 (1984).
Borowy-Borowski et al., "Study of Side Reactions Occurring during Synthesis of Oligodeoxynucleotides Containing O$^6$-Alkyldeoxyguanosine Residues at Preselected Sites," Biochemistry, 26, 2465 (1987).
Kyellberg et al., "Studies on the Alkylation of Derivatives of Guanine," Nucleosides & Nucleotides, 8(2), 225-256 (1989).
Ishido et al., Chem. Abstr., 109:234171q (1988); abstract of PCT Intl. Application WO 88 03,149.
Gladkaya et al., Chem. Abstr., 112:198,947m (1990); Abstract only.
Kochetkov et al., Organic Chemistry of Nucleic Acids, Part B, Plenum Press, New York, 1972, see pp. 458-460.
Takaku et al., Chem. Lett., 1986, 1005-1008.
Rozners et al., Bioorg. Khim., 16(11), 1531-1536 (1990).
Fujii et al., Chem. Pharm. Bull., 35(7), 3066-3069 (1987).
Kamimura et al., Nucleic Acids Research Symposim Series, No. 12, IRL Press Ltd., Oxford England, 1983, pp. 63-65.

Primary Examiner—Johnnie R. Brown
Assistant Examiner—L. Eric Crane
Attorney, Agent, or Firm—Hale and Dorr

[57] ABSTRACT

This invention is directed to N (amino)-protected-2'-O-methyl (methoxy)-5'-dimethoxytrityl (dimethoxytrityl) ribonucleosides (Group I compounds) and to N-protected-2'-O-methyl-5'-dimethoxytrityl-3'-ribonucleoside cyanoethyl N,N-diisopropyl phosphoramidites (Group II compounds). This invention is further directed to the processes involved in producing these compounds. The purification processes produce products in Group I with purity in excess of 99.50% and up to 99.8%. The purity of the products in Group II ranges in excess of 99.8% and up to 99.9%.

3 Claims, 1 Drawing Sheet

N-PROTECTED-2'-O-METHYL-RIBONUCLEOSIDES AND N-PROTECTED 2'-O-METHYL-3'-CYANOETHYL-N-,N-DIISOPROPYL PHOSPHORAMIDITE RIBONUCLEOSIDES

FIELD OF THE INVENTION

This invention relates to 2'-O-methyl ribonucleosides and to their synthesis.

BACKGROUND OF THE INVENTION

One of the goals of molecular biology is to understand the biological information contained in DNA and RNA sequences. The use of synthetic, sequence defined DNA and RNA has played a key role in understanding the genetic code and various regulatory signals such as the operator, promoter, ribosomal binding sites, enhancers, and transposable elements. The synthetic approach not only provides a final proof of the roles of various DNA and RNA sequences but also offers an opportunity for further improvement in function for practical application. The application of synthetic genes, linkers, primers, and probes from both DNA and RNA has become a powerful tool in the cloning, sequencing, and isolation of genomic DNA.

The synthetic methodology for the synthesis of short oligoribonucleotides by the phosphodiester approach was developed in the 1960s by Khorana (Khorana, H. G., *Pure Appl. Chem.* 17: 349–381 (1968)). Organic chemical syntheses of larger molecules of oligoribonucleotides have been attempted by using the phophodiester, phosphotriester, or phosphite triester methods. However, the discovery of RNA ligase has extended the possibilities for synthesizing RNA molecules such as tRNA. Before RNA can be synthesized, however, the starting monomers must be provided. In synthesizing sequence defined RNA oligomers, the purity and correct structure of the monomer building blocks is critical.

Currently reports have been available on the synthesis of N-protected-2'-O-methyl-3'-O-chlorophenyl phosphotriester ribonucleosides (Inoune, H., Hayase, Y., Iwai, S. and Ohtsuka, E., *FEBS Letters*, 215: 327–330 (1987) "Inoune I") and N-protected-2'-O-methyl-3'-cyanoethyl phosphoramidite ribonucleosides (Sproat, B. S., Beijer, B., and Iribarren, A., *Nucl. Acids Res.*, 18: 41–49 (1990)). The methyl iodide/silver oxide method developed by Inoune, et al., I (1987), on the seven membered bis-sililoxy protected (Markiewicz, W. T., *J. Chem. Res.*, (S), 24–25 (1979)) uridine and N6-cytidine generates the undesired 3'-O-methyl-isomers to the extent of 6–8%.

It is believed that methyl iodide in the Inoune method causes the partial ring opening, and subsequently leads to 3'-O-methyl-isomer formation. Similarly, the $CH_2N_2$ reaction under very mild reaction conditions still leads to formation of some 3'-O-methyl isomer (4–5%). This reaction is described in Inoune, et al., I (1987), as well as Ekborg, G. and Garegg, P. J., *J. Carbohyd. Nucleosides and Nucleotides*, 7: 57–61 (1982) and Heikkila, J., Bjorkaman, S., Oberg, B., Chattopadhyaya, J. *Acta. Chem. Scand.*, B36: 715–717 (1982).

It is therefore important to establish stringent purification techniques and a certain homogeneity of the phosphoramidites because of their use in RNA syntheses. In Sproat, B. S., Beijer, B., and Iribarren, A., *Nucl. Acids Res.* 18: 41–49 (1990)), discussing the synthesis of N-protected-2'-O-methyl-3'-cyanoethyl phosphoramidite ribonucleosides, the authors report only a single peak in $^{31}$P-NMR of N2-(4-tertbutyl) benzamido-2'-O-methyl-3'-cyanoethyl phosphoramidite of guanosine.

Since these products are used directly in the synthesis of defined sequence RNA, the purity as well as absolute structure assignment is very critical for any biological application. Besides the concern for purity of these biochemicals, it is also advantageous to develop products which have the most commonly used protecting groups on the pyrimidine or purine ring system of these monomers. This is important for the convenience of the synthesizer and dramatically improves the quality of the 2'-O-methyl-RNA oligomers produced from these monomers. Thus, the $N^2$-isobutyryl group on guanosine and $N^6$-benzoyl on adenosine represent the most versatile protecting group for the aforementioned purposes.

SUMMARY OF THE INVENTION

Figure 1:
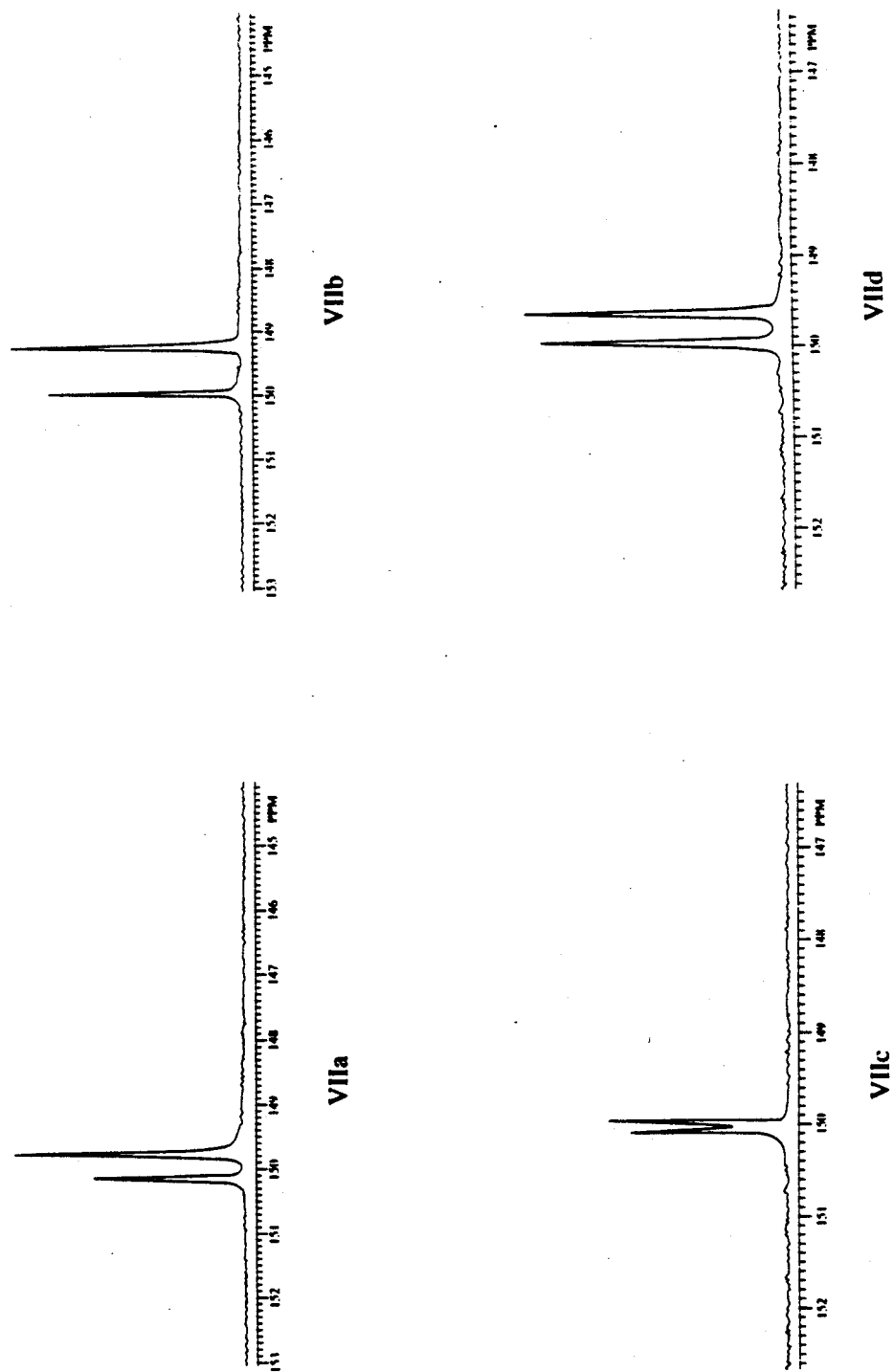
FIG. 1 shows the $^{31}$P-NMR spectra (300 MHz) of the 2'-O-mehtyl nucleoside cyanoethyl phosphoramidites in $CD_bCN$ (VIIa–d).

This invention is directed to processes for producing high purity N-protected-2'-O-methyl-5'-dimethoxytrityl ribonucleosides (Group I). This invention is specifically directed to the compound of Group I, $N^2$-isobutyryl-$O^6$-methyl-2'-O-methyl-5'-dimethoxytrityl-Guanosine (VI).

This invention is also directed to processes for producing high purity N-protected-2'-O-methyl-5'-dimethoxytrityl-3'-ribonucleoside cyanoethyl N,N-diisopropyl phosphoramidites (Group II). This invention is specifically directed to two compounds of Group II: $N^6$-benzoyl-2'-O-methyl-5'-dimethoxytrityl-Adenosine-3'-cyanoethyl-N,N-diisopropyl phosphoramidite (VIIa) and $N^2$-isobutyryl-2'-O-methyl-5 '-dimethoxytrityl-Guanosine-3'-cyanoethyl-N,N-diisopropyl phosphoramidite (VIIc).

The process involved in Group I compounds includes the following five compounds:

$N^6$-benzoyl-2'-O-methyl-5'-dimethoxytrityl-Adenosine (Va);

$N^2$-benzoyl-2'-O-methyl-5'-dimethoxytrityl-Cytidine (Vb);

$N^2$-isobutyryl-2'-O-methyl-5'-dimethoxytrityl-ribo Guanosine (Vc);

2'-O-methyl-5'-dimethoxytrityl Uridine (Vd); and $N^2$-isobutyryl-O-6-methyl-2'-O-methyl-5'-dimethoxytrityl-Guanosine (VI).

The process involved in producing Group II compounds includes the following 4 compounds:

$N^6$-benzoyl-2'-O-methyl-5'-dimethoxytrityl-Adenosine-3'-cyanoethyl-N,N-diisopropyl phosphoramidite (VIIa);

$N^2$-benzoyl-2'-O-methyl-5'-dimethoxytrityl-Cytidine-3'-cyanoethyl-N,N-diisopropyl phosphoramidite (VIIb);

$N^2$-isobutyryl-2'-O-methyl-5'-dimethoxytrityl-Guanosine-3'-cyanoethyl-N,N-diisopropyl phosphoramidite (VIIc); and 2'-O-methyl-5'-dimethoxytrityl-Uridine-3'-cyanoethyl-N,N-diisopropyl phosphoramidite (VIId).

The purification processes produce products in Group I with purity in excess of 99.50% and up to 99.8%. The purity of the products in Group II ranges in excess of 99.8% and up to 99.9%. In addition, the improvement of the reaction conditions as described below in the process parameters reduced the wrong isomer to 3-4%.

DETAILED DESCRIPTION OF THE INVENTION

The reaction scheme for the synthesis of the compounds of this invention are depicted in the schematic representation. The symbols and abbreviations in the schematic follow standard nomenclature: A=Adenosine; G=Guanosine; C=Cytidine; and U=Uridine. The substituients at B or R are represented by standard symbols wherein N=nitrogen; Bz=benzoyl; and iBu=isobutyryl. MMT represents monomethoxytrityl and DMT represents dimethoxytrityl.

Schematic of Figures

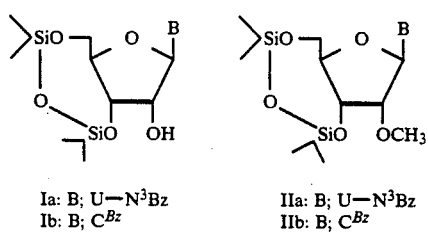

Ia: B; U—N$^3$Bz
Ib: B; C$^{Bz}$

IIa: B; U—N$^3$Bz
IIb: B; C$^{Bz}$

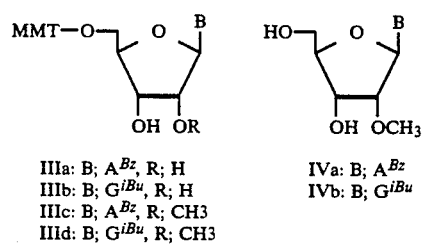

IIIa: B; A$^{Bz}$, R; H
IIIb: B; G$^{iBu}$, R; H
IIIc: B; A$^{Bz}$, R; CH3
IIId: B; G$^{iBu}$, R; CH3

IVa: B; A$^{Bz}$
IVb: B; G$^{iBu}$

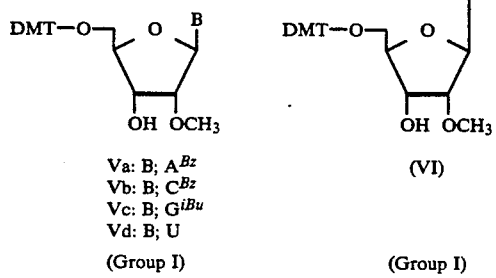

Va: B; A$^{Bz}$
Vb: B; C$^{Bz}$
Vc: B; G$^{iBu}$
Vd: B; U (Group I)

(VI)

(Group I)

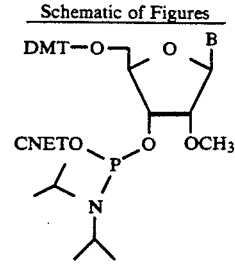

VII a: B; A$^{Bz}$
VII b: B; C$^{Bz}$
VII c: B; G$^{iBu}$
VII d: B; U (Group II)

Methyl Iodide and Silver Oxide Reaction on 3',5'-bis silylated-Uridine (Ia) and Cytidine (Ib) derivatives The starting material, 3',5'-bis silylated-uridine and cytidine, represented by Ia and Ib, respectively, when treated by the methyl iodide/silver oxide reaction at 25° C. for 24-46 hours leads to cleaner conversion products, represented by IIa and IIb, as well as a high rate of conversion (80-86%). Table 1 shows the reaction conditions of the methyl iodide/silver oxide reaction.

TABLE 1

| Compound Quantity | Tolune | Methyl Iodide | Ag2O | Reaction temp & total time | 2'-OMe Product (% isolated) |
|---|---|---|---|---|---|
| Ia 11.85 g | 90 ml | 4.5 ml (72 mm) | 9.75 g (42 mm) | RT; 24 hrs. | IIa 88% |
| Ib 11.6 g (19.6 mm) | 95 ml | 5.0 ml (80 mm) | 13 g (56 mm) | RT; 46 hrs. | IIb 76% |

After the completion of the reaction, the suspension was filtered, filtrate dried in vacuum, co-evaporated several times with toluene. The crude gum was extracted with ethylacetate, washed with saturated NaCl solution, followed by drying and evaporation of the organic layer. The dried foam was column chromatographed with silica gel (grade A) using Hexane and Ethyl Acetate gradient (10-25% Ethyl Acetate).

N$^2$-isobutyryl-5'-monomethoxytrityl Guanosine (IIIb)

N$^6$-benzoyl-5'-monomethoxytrityl Adenosine (IIIa)

The diazomethane reaction was done on N$^2$-isobutyryl-5'-monomethoxytrityl-Guanosine (IIIb), as described by Inoune, et al., II (1987), incorporated herein by reference, however at −10° C., with reaction leading to (IIId). Similar reaction on N$^6$-benzoyl-5'-monomethoxytrityl Adenosine (IIIa), leads to high yields of corresponding 2'-monomethylated products (IIIc), with a minimum contamination of corresponding 3'-O-methyl isomer (6-8%).

The optimized alkylation reaction conditions described above using methyl iodide/silver oxide and diazomethane are crucial to achieving targeted high purity of the desired products.

The processes for producing compound N$^6$-benzoyl-2'-O-methyl-5'dimethyoxytrityl-Adenosine, Va, and N$^2$-isobutyryl-2'-O-methyl-5'dimethoxytrityl-Guinosine, Vc are described in detail. The same procedures are used to produce compounds as shown in Vb and Vd, with the appropriate starting material.

The synthesis of 5'-dimethoxytrityl-2'-O-methyl-Uridine (Vd), N[6]-benzoyl-5'-dimethoxytrityl-2'-O-Me-Cytidine (Vb), and N[2]-isobutyryl-5'-dimethoxytrityl-2'-O-methyl-Guanosine (Vc) were carried out by modifying and improving the method by Inoune, et al., II (1987), incorporated herein by reference.

In general, treatment of purified compounds represented by IIIc and IIId with 80% aqueous acetic acid leads to compounds represented by IVa and IVb. Purification of these products is then done on a silica gel column. Subsequent conversion with dimethoxytritylchloride is followed to lead to corresponding 5'-dimethoxytrityl-2'-O-methyl-Nucleosides (Va and Vc). Chromatography of the reaction mixtures produces these compounds in essentially 100% isomeric and overall purity.

N[6]-benzoyl-2'-O-methyl-5'-dimethoxytrityl-Adenosine (Va)

N[6]-Bz-5'-MMT-A (IIIa, 6.43, 10 mmole) was taken in DMF (400 ml) and SnCl$_2$ (0.4 gm), and the solution was brought to $-10°$ C. Diazomethane made according to the literature procedure (Robins, M. J., Naik, S. R. and Lee, A. S. K., *J. Org. Chem.* 39: 1891–1899 (1974), solution B) (105 ml) was added portion wise during 4 hours, followed by stirring at 15° C. for an additional 2 hours. Aqueous ammonia (5 ml) was added at 0° C., pumped out to remove DMF, followed by extraction with chloroform. The reaction was completed to the extent of 75% from TLC. From 1H-NMR and TLC analysis, approximately 96% of 2'-O-methyl isomer along with 5% of 3'-O-methyl isomer was present. The crude product was purified by column chromatography on silica gel (grade a) using chloroform and a gradient of 1–5% methanol.

The isolated yield of this compound (IIIc) wa 4.670 grams (68%). The total pure isolated compound (IIIc) was treated with 80% aqueous acetic acid (25 ml) for 5 hours at 10° C. with the excess acetic acid pumped out by coevaporation with pyridine several times. The residue was extracted with chloroform, organic layer washed with saturated NaCl solution. The combined organic layer was pumped out. The residue was chromatographed on silica gel column (grade b) using chloroform and gradient of 3–7% methanol. The isolated yield of the product (IVa) was 1.77g (68%). The compound (IVa; 1.75 grams; 4.54 mmole) was thoroughly dried with pyridine several times and taken in dry pyridine (20 ml) and dimethoxytrityl-Cl (2.03g; 6.0 mmole) was added, followed by reaction at room temperature for 5 hours. Workup was done in usual way followed by chromatography as described for the compound, IIIa. The isolated yield of the pure column fractions, product (Va), was 2.02 grams (65%).

N[2]-isobutyryl-2'-0 methyl-5'-dimethoxytrityl-Guanosine (Vc)

The compound (IIIb; 6.43 grams; 10 mmole) was taken in DMF (400 ml) and stannous chloride (0.4 grams) and the solution brought to 10° C. Diazomethane solution was made according to literature method (solution B) as described in Robins, M. J., Naik, S. R. and Lee, A. S. K., *J. Org. Chem.* 39: 1891–1899 (1974).

Solution B was added during the course of 4 hours followed by stirring at $-10°$ C. for additional 2 hours. Aqueous ammonia (5 ml) was added at 0° C., followed by further workup as described above for compound, Va. The ratio of the 2'- and 3'-isomers formed in this reaction was 95:5. The isolated yield of the pure 2'-isomer (99% purity by high resolution 1H-NMR) (IIId) was 4.47 grams (72%). The total pure product (IIId) obtained above was treated with 80% aqueous acetic acid for 3 hours at room temperature. The further workup was done as described above for compound, IVb. The isolated yield of compound, IVb was 3.34 grams (91%). The column purified product (IVb; 3.2 grams; −8.72 mm) was thoroughly dried with pyridine several times, taken in dry pyridine (25 ml) and dimethoxytrityl-Cl (3.08 grams; 9.1 mm), and the reaction was allowed to take place for 4 hours at room temperature. Workup was done as described above for compound, Va. Isolated yield after column chromatography was 5.02 grams (99.9% purity) of product, Vc.

Table 2 shows the RF values of N-Protected-2'-O-methyl-5'-dimethoxytrityl-Ribo Nucleoside of Va–d.

TABLE 2

| RF Values N-Protected-2'-O-methyl-5-'-dimethoxytrityl-Ribo Nucleosides | | |
|---|---|---|
| System; CHCl3:MeOH: 98.5:1.5 | (Va) 0.48 | (Vb) 0.47 |
| System; CHCl3:ETOAC:MeOH:Et3N: 47:47:2.5:3.5 | (Vc) 0.37 | |
| System; CHCl3:MeOH: 98:2 | (Vd) 0.33 | |

Phosphitylation of the compounds (Group I) with (N,N-diisopropyl amino) (cyanoethyl) phosphonamidic chloride was accomplished in high yields. The 2'-O-methyl-3'-Cyanoethyl phosphoramidites of all the four ribonucleosides (VIIa–d) were obtained with the purity in excess of 99.9% after silica gel column chromatography.

N-protected-2'-O-methyl-3'-cyanoethyl-Ribo Nucleoside Phosphoramidites VIIa–d

The precursor compounds (Va–d) were converted to their corresponding 3'-cyanoethyl phosphoramidites (VIIa–d) under the standard conditions described in Scaringe, S. A., Franklyn, C., Usman, N., *Nucl. Acids Res.* 18: 5433–5441 (1990), incorporated by reference. The compounds were purified by silicagel column chromatography (grade A). The gradient system for the elution of products VIIa and VIIb was Hexane:EthylAcetate:Triethylamine :: 45:35–50:10, and for product VIIc was EthylAcetate:Acetone:Triethylamine :: 70:15–25:10. For the product, VIId the gradient system was Hexane:EthylAcetate:Triethylamine :: 20:60–80:10.

Table 3 shows the RF values of N-protected-2'-O-methyl-3'-cyanoethyl-ribonucleoside phosphoramidites, VIIa–d.

TABLE 3

| RF values N-protected-2'-O-methyl-3'-cyanoethyl-ribonucleoside phosphoramidites (VIIa-d) | |
|---|---|
| System: Hexane:ETOAC:ET3N: 45; 45; 10 | (VIIa) 0.51 & 0.40 (VIIb) 0.41 & 0.32 |
| System; ETOAC:Acetone:Et3N: 70:20:10 | (VIIc) 0.45 |
| System; ETOAC:Et3N: 20:70:10 | (VIId) 0.37 & 0.28 |

$^1$H-NMR and $^{31}$P-NMR spectra results were obtained with a Varian 300 MHz spectrometer, and the chemical shifts are expressed in δ values (ppm) relative to TMS as internal standard for $^1$H-NMR and phosphoric acid as external standard for $^{31}$P-NMR. The NMR spectrum of the cyanoethyl-phosphoramidites was done in dry deuterated acetonitrile. Thin layer chromatography was done on Baker-Flex silicagel 1B-F TLC plates (20×20cm). Column chromatography was done with silicagel 60 EM Science, particle size 0.04-0.63 mm (230-400 mesh) (grade a), and particle size 0.063-0.200mm (70-230 mesh) (grade b). Pyridine, reagent grade was first treated with chlorosulfonic acid (1% v/v) at 0° C., distilled followed by storage over KOH pellets (1% w/v), distilled and kept over molecular sieve.

The determination of the detection limit and the establishment of purity of the nucleosides (Va-d), thin layer chromatography (TLC) was used as the criteria. By using high concentrations, it was possible to detect impurities to the extent of 0.25% ±0.10%. For the phosphoramidites (VIIa-d), $^{31}$P-NMR analysis was used to determine the purity. The desired phosphoramidite associated peaks appear as sharp doublets. By taking up to three fold excess (as compared to normal quantity of 15 mg), in CD$_3$CN, in the NMR tube, and increasing the data acquisition time 3 times, it was possible to detect impurities up to the extent of 0.5%.

Table 4 shows the NMR results of N-protected-5'-dimethoxytrityl-2'O-methyl-Ribonucleosides, Vd, Vb, Va, Vc, and VI.

TABLE 4

Proton NMR (300 MHz)* of the N-protected-5'-DMT-2'OMe-RiboNucleosides**

| H-1' | H-2' | H-3' | H-4' | H-5' | H-5" | H-5 | H-6 | DMT-OCH3 | 2'-OCH3 | Aromatic |
|---|---|---|---|---|---|---|---|---|---|---|
| \multicolumn{11}{c}{5'-O-(Dimethoxytrityl)-2'-OMe-Uridine (Vd)} |
| 5.91 | 3.97 | 4.03 | 3.92 | 3.46 | 3.39 | 5.25 | 7.88 | 3.79 | 3.54 | 6.88 |
| — | — | — | — | — | — | — | — | (s) | (s) | — |
| 5.93 | 4.03 | 4.07 | 3.95 | 3.51 | 3.46 | 5.27 | 7.91 | | | 7.52 |
| (d) | (dd) | (m) | (m) | (m) | (m) | (d) | (d) | | | (m) |
| J=2.69 | J=8.0 | | | | | J=8.2 | | | | |
| \multicolumn{11}{c}{N$^4$-Benzoyl-5'-O-(dimethoxytrityl)-2'-OMe-Cytidine (Vb)} |
| 5.88 | 3.98 | 3.99 | 3.81 | 3.48 | 3.34 | 7.13 | 8.47 | 3.79 | 3.63 | 6.88 |
| — | — | — | — | — | — | — | — | (s) | (s) | — |
| 5.88 | 3.99 | 4.03 | 3.83 | 3.50 | 3.48 | 7.16 | 8.49 | | | 7.98 |
| (s) | (dd) | (m) | (m) | (m) | (m) | (d) | (d) | | | (m) |
| J=2.69 | J=9.0 | | | | | J=7.46 | | | | |

| H-1' | H-2' | H-3' | H-4' | H-5' | H-5" | H-2 | H-8 | DMT-OCH3 | 2'-OCH3 | Aromatic |
|---|---|---|---|---|---|---|---|---|---|---|
| \multicolumn{11}{c}{N$^6$-Benzoyl-5" O-(dimethoxytrityl)-2'-OMe-Adenosine (Va)} |
| 6.14 | 4.37 | 4.43 | 4.13 | 3.44 | 3.33 | 8.18 | 8.68 | 3.70 | 3.51 | 6.72 |
| — | — | — | — | — | — | (s) | (s) | (s) | (s) | — |
| 6.15 | 4.41 | 4.48 | 4.18 | 3.49 | 3.38 | | | | | 7.96 |
| (d) | (dd) | (m) | (m) | (m) | (m) | | | | | (m) |
| J=4.15 | J=9.22 | | | | | | | | | |

| H-1' | H-2' | H-3' | H-4' | H-5' | H-5" | | H-8 | DMT-OCH3 | 2'-OCH3 | C—H | CH3 CH3 | C |
|---|---|---|---|---|---|---|---|---|---|---|---|---|
| \multicolumn{13}{c}{N$^2$-Isobutyryl-5'-O-(dimethoxytrityl)-2'OMe-Guanosine (Vc)} |
| 5.91 | 4.30 | 4.54 | 4.06 | 3.36 | 3.25 | — | 7.86 | 3.74 | 3.46 | 2.57 | 1.16 | 6.75 |
| — | — | — | — | — | — | | (s) | (s) | (s) | — | — | — |
| 5.92 | 4.33 | 4.56 | 4.10 | 3.43 | 3.29 | | | | | 2.66 | 1.22 | 7.45 |
| (d) | (dd) | (dd) | (m) | (m) | (m) | | | | | (m) | (m) | (m) |
| J=3.86 | J=5.13 | | | | | | | | | | | |

| H-1' | H-2' | H-3' | H-4' | H-5' | H-5" | | H-8 | DMT-OCH3 | 2'-OCH3 | O-6 OMe | C—H | CH3 CH3 | C |
|---|---|---|---|---|---|---|---|---|---|---|---|---|---|
| \multicolumn{14}{c}{N$^2$-Isobytyryl-O-6-methyl-5'-O-(dimethoxytrityl)-2'-OMe-Guanosine (VI)} |
| 5.99 | 4.43 | 4.69 | 4.04 | 3.39 | 3.22 | — | 8.01 | 3.73 | 4.09 | 3.47 | 2.68 | 1.12 | 6.73 |
| — | — | — | — | — | — | | (s) | (s) | (s) | (s) | — | — | — |
| 6.01 | 4.45 | 4.72 | 4.08 | 3.44 | 3.26 | | | | | | 2.73 | 1.16 | 7.57 |
| (d) | (dd) | (m) | (m) | (m) | (m) | | | | | | (m) | (m) | (m) |

Table 5 shows the proton NMR spectra of the compounds represented by VIIIa-d.

TABLE 5

Proton NMR spectra of the 2'-OMe-Nucleoside CNET Phosphoramidites
(300 MHz)* in CD3CN** (VIIa-d)

| H1' | H2' | H3' | H4' | H5' | H5" | DMT OMe | 2' OMe | —P—O— CH2 | CH2 CN | —NCH Me2 | —N—C— (CH3) | Base Protons | |
|---|---|---|---|---|---|---|---|---|---|---|---|---|---|
| \multicolumn{14}{c}{5'-O-(dimethoxytrityl)-2'-OMe-Uridine-3'CNET-N,N-diisopropyl Phosphoramidite (VIId)} |
| 5.86 | 4.51 | 4.41 | 4.10 | 3.55 | 3.36 | 3.74 | 3.49 | 3.80 | 2.48 | 2.66 | 1.00 | H-5 | H-6 |
| — | — | — | — | — | — | & | & | — | — | — | — | 5.24 | 7.77 |
| 5.89 | 4.61 | 4.98 | 4.20 | 3.69 | 3.48 | 3.73 | 3.51 | 4.00 | 2.52 | 2.70 | 1.38 | — | — |
| (dd) | (m) | (m) | (m) | (m) | (m) | (ts) | (ts) | (m) | (m) | (t) | (m) | 5.30 | 7.91 |
| J=6.83 | | | | | | | | | | | | | |

N$^4$-Benzoyl-5'-O-(dimethoxytrityl)-2'-OMe-Cytidine-3'CNET-N,N,-diisopropyl
Phosphoramidite (VIIb)

TABLE 5-continued

Proton NMR spectra of the 2'-OMe-Nucleoside CNET Phosphoramidites
(300 MHz)* in CD3CN** (VIIa-d)

| | | | | | | | | | | | | H-5 | H-6 |
|---|---|---|---|---|---|---|---|---|---|---|---|---|---|
| 5.89 | 4.43 | 4.58 | 3.91 | 3.52 | 3.41 | 3.78 | 3.59 | 4.18 | 2.48 | 2.65 | 1.12 | 7.02 | 8.42 |
| & | — | — | — | — | — | & | & | — | — | — | — | — | — |
| 5.91 | 4.52 | 4.67 | 4.05 | 3.68 | 3.52 | 3.78 | 3.60 | 4.22 | 2.52 | 2.70 | 1.24 | 7.11 | 8.56 |
| (ts) | | | | | | & | (ts) | (d) | (t) | | | (m) | |
| | | | | | | 3.79 | | | | | | H-2 | H-8 |

N$^6$-Benzoyl-5'-O-(dimethoxytrityl)-2'-OMe-Adenosine-3'CNET-N,N-diisopropyl Phosphoramidite (VIIa)

| 6.13 | 4.66 | 4.74 | 4.26 | 3.58 | 3.27 | 3.73 | 3.45 | 3.76 | 2.48 | 2.65 | 1.12 | 8.27 | 8.58 |
|---|---|---|---|---|---|---|---|---|---|---|---|---|---|
| — | — | — | — | — | — | (ms) | & | — | — | — | — | — | — |
| 6.15 | 4.71 | 4.84 | 4.33 | 3.72 | 3.43 | | 3.47 | 3.89 | 2.52 | 2.70 | 1.21 | 8.30 | 8.60 |
| (d) | (m) | (m) | (m) | (m) | (m) | | (ts) | (m) | (t) | (m) | (m) | (ts) | (ts) |
| | | | | | | | | | | | | H-8 | |

N$^2$-Isobutyryl-5'-O-(dimethoxytrityl)-2'-OMe-Guanosine-3'-N,N-diisopropyl Phosphoramidite (VIIc)

| 5.91 | 4.45 | 4.51 | 4.25 | 3.55 | 3.33 | 3.75 | 3.43 | 3.78 | 2.66 | 2.47 | 1.05 | 7.84 |
|---|---|---|---|---|---|---|---|---|---|---|---|---|
| — | — | — | — | — | — | (ts) | & | — | — | — | — | & |
| 5.93 | 4.50 | 4.55 | 4.31 | 3.68 | 3.42 | | 3.46 | 3.85 | 2.69 | 2.50 | 1.22 | 7.87 |
| (d) | (dd) | (m) | (m) | (m) | (dd) | | (ts) | (m) | (t) | (m) | (m) | (ts) |

Tables 4 and 5:
*except for (Va) in 400 MHz, t: triplet, ms: multiple singlets, ts: two singlet, d: doublet, dd: doublet of doublet, m: multiplet
**internal TMS at 0 ppm Table 6 shows the $^{31}$P-NMR results of 2'-methoxy nucleoside cyanoethyl phosphoramidites, VIIa-d.

TABLE 6

$^{31}$p-NMR (300 MHz)$^a$ of 2'-O-methyl Nucleoside CNEt Phosphoramidites in CD$_3$CN (VIIa-d)

| Frequency | PPM |
|---|---|
| N6-Benzoyl-5'-O-(dimethoxytrityl)2'-OMe-Adenosine-3'-CNEt-N, N-diisopropyl Phosphoramidite (VIIa) | |
| 18226.3 | 150.116 |
| 18183.9 | 149.767 |
| N4-Benzoyl-5'-O-(dimethoxytrityl)-2'-OMe-Cytidine-3'-CNEt-N, N-diisopropyl Phosphoramidite (VIIb) | |
| 18210.4 | 149.985 |
| 18125.3 | 149.284 |
| N2-Isobutyryl-5'-(dimethoxytrityl)-2'-OMe-Guanosine-3'-CNEt-N, N-diisopropyl Phosphoramidite (VIIc) | |
| 18223.3 | 150.082 |
| 18208.0 | 149.965 |
| 5'-O-(dimethoxytrityl)-2'-OMe-Uridine-3'-CNEt-N,N-diisopropyl Phosphoramidite (VIId) | |
| 18210.1 | 149.982 |
| 18167.7 | 149.633 |

The results show that using process of this invention, N-protected-5'-dimethoxytrityl-2'-O-methyl-nucleosides of common ribonucleosides can be prepared with a purity in excess of 99.8%. The corresponding 3'-cyanoethyl phosphoramidites can be prepared with purity greater than 99.9%. The coupling efficiency of these phosphoramidites was >99% with the coupling time of 2.5 minutes and the total cycle time being 7.5 minutes, using 1H-tetrazole.

The 2'-O-Methyl oligoribonucleotides of this invention can be used as chimeric oligomers with DNA-oligomers for site directed cleavage of RNA with Rnase H (Inoune, et al. I (1987) and Shibahara, S., Mukai, S., Nishihara, T., Inoune, H., Ohtsuka, E. and Morisawa, H., Nucl. Acids Res 15: 4403-4415 (1987)).

These oligoribonucleotides, oligo (2'-O-methyl) ribonucleotides, are more stable against several nucleases as compared to deoxy and ribo-oligonucleotides. Nucleases generally degrade both deoxy and ribo type of oligomers. Therefore, the 2'-O-methyl oligoribonucleotides are less susceptible to several nucleases (Dunlap, B. F., Friderici, K. H., Rottman, F., *Biochemistry* 10: 2581-2587 (1971)).

Using O-methyl and mixed phosphorothioates results in an inhibitory effect against HIV induced cytopathic effect and expression of the virus specific antigens in cultured MT-4 cells as reported in Shibahara, S., Mukai, S., Morisawa, H., Nakashima, H., Kobayashi, S., Yamamoto, N., *Nucl. Acids Res.* 17: 239-252 (1989), thus indicating an area for therapeutics against the retrovirus. In this study, the antiviral activity seems to be strongly concerned with the resistance to one or the other kind of deoxynucleases.

Unidirectional deletion of DNA by Bal 31 nuclease (Mukai, S., Shibahara, H., Morisawa, H., *Nucl. Acids Res., Symposium Series No.* 19: 117-120 (1988)). This emphasizes the nuclease resistance properties of these oligonucleotides.

Using olio (2'-O-methyl) ribonucleotides forms stable heteroduplexes with the complementary RNA. The hybrid formed has a high, or a higher, Tm than the corresponding DNA sequence. (Inoune, H., Hayase, Y., Imura, A., Iwai, S., Miura, K., Ohtsuka, E., *Nucl. Acids Res.* 15: 6131-6148 (1987)).

The ribonucleosides of this invention can also be used as valuable antisense probes for studying pre-mRNA splicing and the structure of spliceosomes (Lamond, A. I., Sproat, B. S., Ryder, U., Hamm, J., *Cell* 58: 383-390 (1989); Barbino, S., Sproat, B. S., Ryder, U., Blencowe, B. J., and Lamond, A. I., *EMBO Journal,* 8,4171-4178 (1989); Blencowe, B. J., Sproat, B. S., Ryder, U., Barabino, S., and Lamond, A. I., *Cell* (1989) 59:531-539 (1989).

The 2'-O-methylethers of common ribonucleosides have been found as minor components of RNA. (R. H. Hall, "The Modified Nucleosides in Nucleic Acids," Columbia University Press, New York, NY., (1971)). Cotton, M., Oberhauser, B., Brunar, H., Holzner, A., Issakides, G., Noe, C. R., Schaffner, G., Wagner, E., and Birnstiel, M. L., *Nucl. Acids Res.,* 19: 2629-2635 (1991).

Although the foregoing invention has been described in some detail by way of illustration and example for purposes of clarity of understanding, it will be obvious to one skilled in the art that certain changes and modifications may be practiced within the scope of the appended claims.

What is claimed is:

1. $N^2$-isobutyryl-$O^6$-methyl-2'-O-methyl-5'-dimethoxytritylguanosine.

2. $N^6$-benzoyl-2'-O-methyl-5'-dimethoxytrityl-adenosine-3'-cyanoethyl-N,N-diisopropyl phosphoramidite.

3. $N^2$-isobutyryl-2'-O-methyl-5'-dimethoxytrityl-3'-guanosine-3'-cyanoethyl-N,N-diisopropyl phosphoramidite.

* * * * *